(12) United States Patent
Creekmore et al.

(10) Patent No.: US 6,316,460 B1
(45) Date of Patent: Nov. 13, 2001

(54) PHARMACEUTICAL COMPOSITIONS

(75) Inventors: Joseph R Creekmore; Norman A. Wiggins, both of Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/633,064

(22) Filed: Aug. 4, 2000

(30) Foreign Application Priority Data

Jan. 26, 2000 (GB) .................................................. 0001621

(51) Int. Cl.⁷ ........................ A61K 31/505; A61K 31/19
(52) U.S. Cl. ........................ 514/275; 514/256; 514/557
(58) Field of Search .................................. 514/557, 256, 514/275

(56) References Cited

U.S. PATENT DOCUMENTS

| | | |
|---|---|---|
| 4,743,450 | 5/1988 | Harris et al. . |
| 5,260,440 | 11/1993 | Hirai et al. . |
| 5,356,896 | 10/1994 | Kabadi et al. . |
| 5,665,881 | 9/1997 | Inoue et al. . |
| 5,686,104 | 11/1997 | Mills et al. . |
| 6,150,410 | 11/2000 | Engh et al. . |

FOREIGN PATENT DOCUMENTS

| | | |
|---|---|---|
| 0 336 298 | 3/1988 | (EP) . |
| 0 380 021 | 8/1990 | (EP) . |
| 0 475 482 A1 | 3/1992 | (EP) . |
| 0 521 471 | 1/1993 | (EP) . |
| 2 262 229 | 6/1993 | (GB) . |
| WO 97/23200 | 7/1997 | (WO) . |
| WO 99/62560 | 12/1999 | (WO) . |
| WO 00/35425 | 6/2000 | (WO) . |
| WO 00/42024 | 7/2000 | (WO) . |
| WO 00/45817 | 8/2000 | (WO) . |
| WO 00/45818 | 8/2000 | (WO) . |
| WO 00/45819 | 8/2000 | (WO) . |

OTHER PUBLICATIONS

Remington's Pharmaceutical Sciences, 13th Ed., 1965, left–hand column, lines 25–27.

*Primary Examiner*—Zohreh Fay
*Assistant Examiner*—Brian-Yong Kwon
(74) *Attorney, Agent, or Firm*—Pillsbury Winthrop LLP

(57) ABSTRACT

The invention concerns a pharmaceutical composition comprising the HMG CoA reductase inhibitor (E)-7-[4-(4-fluorophenyl)-6-isopropyl-2-[methyl(methylsulfonyl)amino]pyrimidin-5-yl]-(3R,5S)-3,5-dihydroxyhept-6-enoic acid or a pharmaceutically acceptable salt thereof as the active ingredient, which remains stable over a prolonged period.

18 Claims, No Drawings

PHARMACEUTICAL COMPOSITIONS

CROSS-REFERENCES TO RELATED APPLICATIONS

Not Applicable

STATEMENT REGARDING FEDERALLY SPONSORED RESEARCH OR DEVELOPMENT

Not Applicable.

BACKGROUND OF THE INVENTION

1. Field of the Invention

The present invention relates to pharmaceutical compositions and more particularly to a pharmaceutical composition containing (E)-7-[4-(4-fluorophenyl)-6-isopropyl-2-[methyl(methylsulfonyl)amino]pyrimidin-5-yl]-(3R,5S)-3,5-dihydroxyhyhept-6-enoic acid or a pharmaceutically acceptable salt thereof (and referred to hereinafter as "the Agent"), in particular the sodium and calcium salts, and especially the calcium salt, bis[(E)-7-[4-(4-fluorophenyl)-6-isopropyl-2-[methyl(methylsulfonyl)amino]pyrimidin-5-yl]-(3R,5S)-3,5-dihydroxyhept-6-enoic acid] calcium salt (of the formula I hereinafter).

2. Description of the Related Art

The Agent is disclosed as an inhibitor of 3-hydroxy-3-methylglutaryl CoA reductase (HMG CoA reductase) in European Patent Application, Publication No. 0521471 and in Bioorganic and Medicinal Chemistry, (1997), 5(2), 437–444 and is useful in the treatment of hypercholesterolemia, hyperlipidproteinemia and atherosclerosis.

A problem associated with the Agent is that it undergoes degradation under certain conditions. This makes it difficult to formulate the product and provide a pharmaceutical composition with adequate storage life. The major degradation products formed are the corresponding (3R,5S) lactone (hereinafter referred to as "the lactone") and an oxidation product (hereinafter referred to as "B2") in which the hydroxy group adjacent to the carbon-carbon double bond is oxidised to a ketone functionality.

It is therefore important to find a pharmaceutical composition of the Agent which remains stable over a prolonged period. It is also preferable that such a composition has a good flow rate to assist processing into unit dosage forms for oral administration, for example into tablets, and good disintegration and dissolution characteristics when processed into tablets for oral administration, which tablets can be in different dosage strengths. It is also desirable that such tablets are of a convenient size for ease of administration.

Pharmaceutical formulations of certain 7-substituted-3,5-dihydroxy-6-heptenoic acid salts, which are HMG CoA reductase inhibitors, are disclosed in UK Patent 2262229.

These formulations require the presence of an alkaline medium (such as a carbonate or bicarbonate) capable of imparting a pH of at least 8 to an aqueous solution or dispersion of the composition.

BRIEF SUMMARY OF THE INVENTION

We have now discovered a novel pharmaceutical composition of the Agent which has advantageous properties and which solves one or more of the problems associated with formulation of the Agent.

Accordingly, a first aspect of the invention comprises a pharmaceutical composition comprising the Agent and a tribasic phosphate salt in which the cation is multivalent.

A second aspect of the invention comprises the use of a tribasic phosphate salt in which the cation is multivalent to stabilise the Agent.

DETAILED DESCRIPTION OF THE INVENTION

A tribasic phosphate salt in which the cation is multivalent includes, for example, tribasic calcium phosphate, tribasic magnesium phosphate and tribasic aluminum phosphate. Tribasic calcium phosphate is especially preferred.

The ratio of tribasic phosphate salt to Agent in the pharmaceutical composition is, for example, within the range of 1:80 to 50:1 by weight, for example 1:50 to 50:1 by weight, such as 1:10 to 10:1 by weight, and more particularly 1:5 to 10:1by weight.

Preferably the pharmaceutical composition of the invention is formulated into an oral dosage form, such as a tablet. Accordingly a further aspect of the invention comprises a pharmaceutical composition comprising the Agent, a tribasic phosphate salt in which the cation is multivalent, and one or more fillers, binders, disintegrates or lubricants. A still further aspect of the invention relates to a pharmaceutical composition for oral administration comprising the Agent, one or more fillers, one or more binders, one or more disintegrates, one or more lubricants and a tribasic phosphate salt in which the cation is multivalent.

Suitable fillers include, for example, lactose, sugar, starches, modified starches, mannitol, sorbitol, inorganic salts, cellulose derivatives (e.g. microcrystalline cellulose, cellulose), calcium sulfate, xylitol and lactitol.

Suitable binders include, for example, polyvinylpyrrolidone, lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatin and sodium alginate.

Suitable disintegrates include, for example, crosscarmellose sodium, crospovidone, polyvinylpyrrolidone, sodium starch glycollate, corn starch, microcrystalline cellulose, hydroxypropyl methylcellulose and hydroxypropyl cellulose.

Suitable lubricants include, for example, magnesium stearate, stearic acid, palmitic acid, calcium stearate, talc, carnauba wax, hydrogenated vegetable oils, mineral oil, polyethylene glycols and sodium stearyl fumarate.

Additional conventional excipients which may be added include preservatives, stabilisers, anti-oxidants, silica flow conditioners, antiadherents or glidants.

Other suitable fillers, binders, disintegrates, lubricants and additional excipients which may be used are described in *Handbook of Pharmaceutical Excipients*, $2^{nd}$ Edition, American Pharmaceutical Association; *The Theory and Practice of Industrial Pharmacy*, $2^{nd}$ Edition, Lachman, Leon, 1976; *Pharmaceutical Dosage Forms*: Tablets Volume 1, $2^{nd}$ Edition, Lieberman, Hebert A., et al, 1989; *Modern Pharmaceutics*, Banker, Gilbert and Rhodes, Christopher T, 1979; and *Remington's Pharmaceutical Sciences*, $15^{th}$ Edition, 1975.

Typically the Agent will be present in an amount within the range of 1 to 50%, and preferably from 1 to 20% (especially 2 to 15%) by weight of the composition.

Typically the tribasic phosphate salt, such as tribasic calcium phosphate, will be present in an amount within the range of 1 to 50%, for example 1 to 25%, such as 1 to 20%, and particularly 5 to 18% by weight.

Typically one or more fillers will be present in an amount 30 to 90% by weight.

Typically one or more binders will be present in an amount 2 to 90% by weight.

Typically one or more disintegrates will be present in an amount 2 to 10%, and especially 4 to 6% by weight.

It will be appreciated that a particular excipient may act as both a binder and a filler, or as a binder, a filler and a disintegrant. Typically the combined amount of filler, binder and disintegrant comprises, for example, 70 to 90% by weight of the composition.

Typically one or more lubricants will be present in an amount 0.5 to 3%, and especially 1 to 2% by weight.

Preferred compositions of the invention include, for example, those comprising the Agent, tribasic calcium phosphate and excipients selected from lactose, mannitol, microcrystalline cellulose, povidone, crospovidone, sodium starch glycollate and magnesium stearate. Preferred independent compositions of the invention include, for example, compositions comprising the Agent, tribasic calcium phosphate, microcrystalline cellulose, lactose, sodium starch glycollate, butylated hydroxytoluene and magnesium stearate; compositions comprising the Agent, povidone, tribasic calcium phosphate, microcrystalline cellulose, mannitol, sodium starch glycollate, butylated hydroxytoluene and magnesium stearate; compositions comprising the Agent, tribasic calcium phosphate, crospovidone, microcrystalline cellulose, lactose and magnesium stearate, and compositions comprising the Agent, povidone, tribasic calcium phosphate, microcrystalline cellulose, lactose, sodium starch glycollate, magnesium stearate and butylated hydroxytoluene. Where lactose and microcrystalline cellulose are used, these are preferably present in the ratio of about 1:1 to 3:1 by weight.

Compositions of the invention which are of particular interest include, for example, the specific embodiments set out hereinafter in the accompanying Examples.

The pharmaceutical composition of the invention may be prepared, using standard techniques and manufacturing processes generally known in the art, for example by dry blending the components. For example, the Agent, the tribasic phosphate salt (for example tribasic calcium phosphate), one or more fillers, one or more binders and one or more disintegrates, as well as other additional excipients if desired are blended together. The components of the blend prior to blending, or the blend itself, may be passed through a mesh screen, for example a 400–700 um mesh screen. A lubricant, which may also be screened, is then added to the blend and blending continued until a homogeneous mixture is obtained. The mixture is then compressed into tablets. Alternatively, a wet granulation technique can be employed. For example, the Agent, the tribasic phosphate salt, one or more fillers, one or more binders and a portion of a disintegrant, as well as other additional excipients if desired, are blended together, for example by using a granulator, and the powder blend is granulated with a small volume of purified water. The granulate is dried and passed though a mill. The remainder of the disintegrant and a lubricant are added to the milled granulation and after blending the resultant homogeneous mixture is compressed into tablets. It will be appreciated that modifications of the dry blending and wet granulation techniques, including the order of addition of the components and their screening and blending prior to compression into tablets, may be carried out according to principles well known in the art.

A tablet coating may then be applied, for example by spray-coating. With a water-based film coating formulation. The coating may comprise, for example, lactose, hydroxypropyl methylcellulose, triacetin, titanium dioxide and ferric oxides. Coating ingredient combinations are commercially available, such as those described in the Examples hereinafter. The coating may comprise, for example, 0.5 to 10% by weight of the tablet composition, particularly 1 to 6%, and preferably 2 to 3%. Coatings containing ferric oxides are especially preferred as they reduce the rate of formation of photodegradation products of the Agent.

A further aspect of the present invention comprises a method of preparing a stabilised pharmaceutical composition which comprises admixing the Agent with a tribasic phosphate salt in which the cation is multivalent. A further aspect of the present invention comprises a method of producing a stabilised pharmaceutical composition which comprises incorporating a tribasic phosphate salt in which the cation is multivalent in a pharmaceutical composition containing the Agent.

The following pharmaceutical compositions, wherein the Agent is the calcium salt of formula I, are intended to illustrate the invention without being limitative in any way.

EXAMPLE 1

| | |
|---|---|
| The Agent | 2.50 mg |
| Tribasic calcium phosphate | 20.0 mg |
| Microcrystalline cellulose | 47.0 mg |
| Lactose monohydrate | 47.0 mg |
| Sodium starch glycollate | 3.00 mg |
| Butylated hydroxytoluene | 0.05 mg |
| Magnesium stearate | 1.00 mg |

The Agent, microcrystalline cellulose, lactose monohydrate, sodium starch glycolate, tribasic calcium phosphate, and butylated hydroxytoluene were blended together for 10 minutes. Magnesium stearate was screened through a #40 mesh (425 um) screen and added to the blend and blending continued for a further three minutes. The resulting homogeneous mixture was compressed into tablets.

The tablets were stored at 70° C./80% relative humidity for one week. After one week there was found to be only 0.11% w/w of the oxidation product B2 formed and only 0.50% w/w of the lactone. By comparison a similar formulation in which 20.0 mg of tribasic calcium phosphate was replaced by 20.0 mg of dibasic calcium phosphate, 0.23% w/w of B2 was formed and 15.61% w/w of the lactone.

EXAMPLE 2

| | |
|---|---|
| The Agent | 2.50 mg |
| Povidone | 2.50 mg |
| Tribasic calcium phosphate | 20.0 mg |
| Microcrystalline cellulose | 47.0 mg |
| Mannitol | 47.0 mg |
| Sodium starch glycollate | 3.00 mg |
| Butylated hydroxytoluene | 0.05 mg |
| Magnesium stearate | 1.00 mg |

The Agent, povidone, mannitol, microcrystalline cellulose, butylated hydroxytoluene, tribasic calcium phosphate and sodium starch glycollate (in the amounts given above) were blended for 5 to 60 minutes. Magnesium stearate was screened through a #40 mesh (425 um) screen and added to the blend and blending continued for a further three minutes. The resulting homogeneous mixture was compressed into tablets. The compressed tablets were coated by spraying with a mixture of hydroxypropyl methylcellulose, polyethylene glycol 400, titanium dioxide and ferric oxide (sold as Spectrablend by Warner-Jenkinson) and water in a coating pan. The weight gain provided by the coating was 1 to 6% w/w, and preferably 2 to 3% w/w.

The tablets were stored at 70° C./80% relative humidity for one week. After one week here was found to be only 0.06% w/w of the oxidation product B2 formed and only 2.22% w/w of the lactone.

EXAMPLE 3

| | |
|---|---|
| The Agent | 2.60 mg |
| Crospovidone | 3.75 mg |
| Tribasic calcium phosphate | 5.66 mg |
| Microcrystalline cellulose | 15.5 mg |
| Lactose monohydrate | 46.5 mg |
| Magnesium stearate | 0.94 mg |

The Agent and crospovidone were blended together for 5 minutes and the blend then passed through a 400–700 um screen. A small portion of the microcrystalline cellulose was passed through the screen afterwards. The screened material was blended with the other ingredients, excluding the lubricant, for 10 minutes. Magnesium stearate was passed through a #40 mesh (425 um) screen and added to the blend and the mixture was blended for a further 3 minutes. The resulting homogeneous mixture was compressed into tablets. The compressed tablets were coated by spraying with a mixture of lactose monohydrate, hydroxypropyl methylcellulose, triacetin and ferric oxide (sold as Opadry II by Colorcon) and water in a coating pan. The weight gain provided by the coating 1 to 6% w/w, and preferably 2 to 3% w/w.

The tablets were stored at 70° C./80% relative humidity for one week. After this time only 0.19% w/w of the oxidation product B2 had formed and only 2.71% w/w of the lactone.

EXAMPLE 4

| | |
|---|---|
| The Agent | 2.50 mg |
| Povidone | 2.50 mg |
| Tribasic calcium phosphate | 20.0 mg |
| Microcrystalline cellulose | 34.5 mg |
| Lactose monohydrate | 34.0 mg |
| Sodium starch glycollate | 6.00 mg |
| Magnesium stearate | 1.00 mg |
| Butylated hydroxytoluene | 0.05 mg |

A portion of the tribasic calcium phosphate and butylated hydroxytoluene were blended for 30 seconds in a bag. The Agent, povidone, remainder of the tribasic calcium phosphate, microcrystalline cellulose, lactose monohydrate, tribasic calcium phophate/butylated hydroxytoluene mixture and a portion of the sodium starch glycolate were blended in a granulator for 30 seconds. The powder blend was granulated with purified water for 1 minute at the addition rate of 70 mg/tablet/minute. The granulation is dried in a fluidized bed drier at 50° C. until the loss on drying is less than 2% w/w. The dried granulation is passed through a mill (e.g. Comil). The milled granulation and the remainder of the sodium starch glycolate was blended for approximately 5 minutes. Magnesium stearate was screened through a #40 mesh (425 um) screen and added to the blend and blending continued for a further three minutes. The resulting homogeneous mixture was compressed into tablets.

The tablets were stored at 70° C./80% relative humidity for one week. After this time only 0.23% w/w of the oxidation product B2 had formed and only 0.28% w/w of the lactone. by comparison a similar formulation in which 20.0 mg of tribasic calcium phosphate was replaced by 20.0 mg of dibasic calcium phosphate, 0.19% w/w of B2 was formed and 28.15% w/w of the lactone.

Formula 1

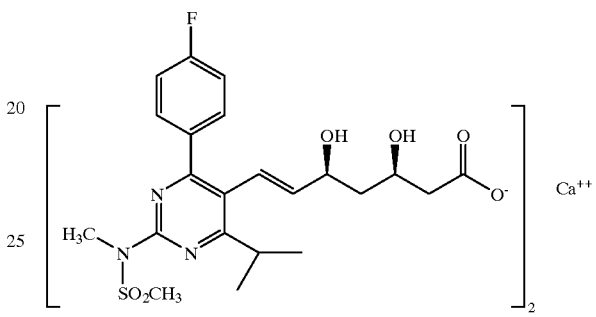

What we claim is:

1. A pharmaceutical composition comprising (E)-7-[4-(4-fluorophenyl)-6-isopropyl-2-[methyl(methylsulfonyl)amino]pyrimidin-5-yl]-(3R,5S)-3,5-dihydroxyhept-6-enoic acid or a pharmaceutically acceptable salt thereof as the active ingredient and a tribasic phosphate salt in which the cation is multivalent.

2. The pharmaceutical composition as claimed in claim 1 wherein the tribasic phosphate salt in which the cation is multivalent is selected from the group consisting of tribasic calcium phosphate, tribasic magnesium phosphate and tribasic aluminum phosphate.

3. The pharmaceutical composition as claimed in claim 1 or 2 wherein the tribasic phosphate salt in which the cation is multivalent is tribasic calcium phosphate.

4. The pharmaceutical composition as claimed in claim 1 or 2 wherein the ratio of the tribasic phosphate salt to the active ingredient is in the range of 1:80 to 50:1 by weight.

5. The pharmaceutical composition as claimed in claim 1 or 2 additionally comprising one or more fillers, binders, disintegrates or lubricants.

6. A pharmaceutical composition for oral administration comprising (E)-7-[4-(4-fluorophenyl)-6-isopropyl-2-[methyl(methylsulfonyl)amino]pyrimidin-5-yl]-(3R,5S)-3,5-dihydroxyhept-6-enoic acid or a pharmaceutically acceptable salt thereof as the active ingredient, one or more fillers, one or more binders, one or more disintegrants, one or more lubricants and a tribasic phosphate salt in which the cation is multivalent.

7. The pharmaceutical composition as claimed in claim 6 wherein the active ingredient is present in an amount 1 to 80% by weight of the composition.

8. The pharmaceutical composition as claimed in claim 6 or 7 wherein the tribasic phosphate salt is present in an amount 1 to 50% by weight of the composition.

9. The pharmaceutical composition as claimed in claim 6 or 7 wherein the filler is present in an amount 30 to 90% by weight of the composition.

10. The pharmaceutical composition as claimed in claim 6 or 7 wherein the binder is present in an amount 2 to 90% by weight of the composition.

11. The pharmaceutical composition as claimed in claim 6 or 7 wherein the disintegrant is present in an amount 2 to 10% by weight of the composition.

12. The pharmaceutical composition as claimed in claim 6 or 7 wherein the lubricant is present in an amount 0.5 to 3% by weight.

13. A pharmaceutical composition comprising (E)-7-[4-(4-fluorophenyl)-6-isopropyl-2-[methyl(methylsulfonyl) amino]pyrimidin-5-yl]-(3R,5S)-3,5-dihydroxyhept-6-enoic acid or a pharmaceutically acceptable salt thereof as the active ingredient, tribasic calcium phosphate, microcrystalline cellulose, lactose, sodium starch glycollate, butylated hydroxytoluene and magnesium stearate.

14. A pharmaceutical composition comprising (E)-7-[4-(4-fluorophenyl)-6-isopropyl-2-[methyl(methylsulfonyl) amino]pyrimidin-5-yl]-(3R,5S)-3,5-dihydroxyhept-6-enoic acid or a pharmaceutically acceptable salt thereof as the active ingredient, tribasic calcium phosphate, povidone, microcrystalline cellulose, mannitol, sodium starch glycollate, butylated hydroxytoluene and magnesium stearate.

15. A pharmaceutical composition comprising (E)-7-[4-(4-fluorophenyl)-6-isopropyl-2-[methyl(methylsulfonyl) amino]pyrimidin-5-yl]-(3R,5S)-3,5-dihydroxyhept-6-enoic acid or a pharmaceutically acceptable salt thereof as the active ingredient, tribasic calcium phosphate, crospovidone, microcrystalline cellulose, lactose and magnesium stearate.

16. A pharmaceutical composition comprising (E)-7-[4-(4-fluorophenyl)-6-isopropyl-2-[methyl(methylsulfonyl) amino]pyrimidin-5-yl]-(3R,5S)-3,5-dihydroxyhept-6-enoic acid or a pharmaceutically acceptable salt thereof as the active ingredient, tribasic calcium phosphate, povidone, microcrystalline cellulose, lactose, sodium starch glycollate, butylated hydroxytoluene and magnesium stearate.

17. The pharmaceutical composition as claimed in claim 1, 2, 6, 13, 14, 15 or 16 wherein the active ingredient is the calcium salt of (E)-7-[4-(4-fluorophenyl)-6-isopropyl-2-[methyl(methylsulfonyl)amino]pyrimidin-5-yl]-(3R,5S)-3,5- dihydroxyhept-6-enoic acid.

18. A method of producing a stabilised pharmaceutical composition, said method comprising the step of incorporating a tribasic phosphate salt in which the cation is multivalent in a pharmaceutical composition containing the compound (E)-7-[4-(4-fluorophenyl)-6-isopropyl-2-[methyl (methylsulfonyl)amino]pyrimidin-5-yl]-(3R,5S)-3,5-dihydroxyhept-6-enoic acid or a pharmaceutically acceptable salt thereof.

* * * * *